US010031024B2

(12) United States Patent
Pope et al.

(10) Patent No.: US 10,031,024 B2
(45) Date of Patent: Jul. 24, 2018

(54) EVALUATING HYDROLOGIC RESERVOIR CONSTRAINT IN COAL SEAMS AND SHALE FORMATIONS

(75) Inventors: John Pope, Laramie, WY (US); Daniel Buttry, Tempe, AZ (US)

(73) Assignee: GAS SENSING TECHNOLOGY CORP., Laramie, WY (US)

( * ) Notice: Subject to any disclaimer, the term of this patent is extended or adjusted under 35 U.S.C. 154(b) by 968 days.

(21) Appl. No.: 14/046,953

(22) PCT Filed: Apr. 5, 2012

(86) PCT No.: PCT/US2012/032300
§ 371 (c)(1),
(2), (4) Date: Oct. 5, 2013

(87) PCT Pub. No.: WO2012/138843
PCT Pub. Date: Oct. 11, 2012

(65) Prior Publication Data
US 2014/0039794 A1    Feb. 6, 2014

Related U.S. Application Data

(60) Provisional application No. 61/472,623, filed on Apr. 7, 2011.

(51) Int. Cl.
*G01J 3/44*    (2006.01)
*G01V 9/00*    (2006.01)
(Continued)

(52) U.S. Cl.
CPC ............... *G01J 3/44* (2013.01); *G01V 9/007* (2013.01); *E21B 49/00* (2013.01); *G01N 21/65* (2013.01)

(58) Field of Classification Search
CPC ............ G01N 21/65; E21B 49/00; G01J 3/44; G01V 9/007
(Continued)

(56) References Cited

U.S. PATENT DOCUMENTS 3,239,666 A    3/1966  Newton
5,684,580 A *  11/1997 Cooper ............. G01N 33/2835
                                                 356/301
(Continued)

OTHER PUBLICATIONS

Patent Cooperation Treaty; PCT Search Report; dated Jun. 15, 2012; pp. 1-12; Alexandria, Virginia.
(Continued)

*Primary Examiner* — Gregory J Toatley
*Assistant Examiner* — Terence Stifter, Jr.
(74) *Attorney, Agent, or Firm* — Adolph Locklar (57) ABSTRACT

Methods and apparatus suitable for quickly and accurately measuring $^{13}C$ levels and supporting data in an aqueous fluid reservoir. Interpreting the resulting data to indicate key factors regarding a reservoir and completion methods, including reservoir constraint, gas producibility, and completion success. A sensor and to a sensing method that evaluates the level of hydrologic constraint in aquifers occurring in unconventional reservoirs, such as shales and coals is disclosed. Specifically, Raman spectroscopy is disclosed as a sensor and a sensing method that measures the level of naturally-occurring $^{13}C$ in an aqueous reservoir and compares the level of $^{13}C$ to the levels typical for highly constrained and highly unconstrained reservoirs. The disclosed sensor and sensing method also monitors the level of naturally-occurring $^{13}C$ in a reservoir. Also disclosed is a method of using $\delta^{13}C_{Dic}$ to evaluate geographic areas of coal bed reservoir water having biologic methanogenic activity.

9 Claims, 6 Drawing Sheets

Raman shift (cm⁻¹)

(51) Int. Cl.
  *G01N 21/65* (2006.01)
  *E21B 49/00* (2006.01)
(58) Field of Classification Search
  USPC .......................................................... 702/8
  See application file for complete search history.

(56) References Cited

U.S. PATENT DOCUMENTS

| | | | | |
|---|---|---|---|---|
| 6,018,389 | A * | 1/2000 | Kyle | G01J 3/02 |
| | | | | 356/301 |
| 6,678,050 | B2 | 1/2004 | Pope et al. | |
| 7,933,718 | B2 * | 4/2011 | McDaniel | E21B 43/26 |
| | | | | 175/40 |
| 2003/0048450 | A1 * | 3/2003 | Pope | G01J 3/28 |
| | | | | 356/435 |
| 2003/0053049 | A1 * | 3/2003 | Fink | G01J 3/44 |
| | | | | 356/301 |
| 2005/0007583 | A1 * | 1/2005 | DiFoggio | G01V 8/02 |
| | | | | 356/301 |
| 2006/0240572 | A1 * | 10/2006 | Carron | G01N 21/658 |
| | | | | 436/524 |
| 2008/0111064 | A1 * | 5/2008 | Andrews | G01V 8/02 |
| | | | | 250/269.1 |
| 2009/0288881 | A1 * | 11/2009 | Mullins | E21B 7/04 |
| | | | | 175/50 |
| 2010/0089142 | A1 * | 4/2010 | Sukhija | C09K 8/58 |
| | | | | 73/152.39 |
| 2010/0224365 | A1 * | 9/2010 | Abad | E21B 43/26 |
| | | | | 166/275 |
| 2010/0228485 | A1 * | 9/2010 | Betancourt | G01V 11/00 |
| | | | | 702/13 |
| 2010/0326651 | A1 * | 12/2010 | Pietrobon | E21B 43/14 |
| | | | | 166/250.01 |
| 2011/0017458 | A1 * | 1/2011 | East, Jr. | E21B 43/26 |
| | | | | 166/308.1 |
| 2011/0297370 | A1 * | 12/2011 | Michael | E21B 47/10 |
| | | | | 166/250.15 |
| 2012/0036923 | A1 * | 2/2012 | Valentine | G01N 33/225 |
| | | | | 73/152.02 |

OTHER PUBLICATIONS

Dudley D. Rice, George E. Claypool, "Generation, Accumulation, and Resource Potential of Biogenic Gas"; AAPG Bulletin, vol. 65, Issue 1. (January), pp. 5-25 (1981).

Anna M. Martini, Klaus Nusslein, Steven T. Petsch, "Enhancing Microbial Gas From Unconventional Reservoirs: Geochemical and Microbiological Characterization of Methane-Rich Fractured Black Shales", Final Report (Mar. 2004-Sep. 2004), Prepared for: Research Partnership to Secure Energy for America, Subcontract No. R-520).

John M. Pope et al., "In-Situ Detection and Analysis of Methane in Coal Bed Methane Formations With Spectrometers", U.S Appl. No. 61/602,939, filed Feb. 24, 2012.

* cited by examiner

EVALUATING HYDROLOGIC RESERVOIR CONSTRAINT IN COAL SEAMS AND SHALE FORMATIONS

RELATED APPLICATIONS

This application claims priority to U.S. Provisional Application Ser. No. 61/472,623 entitled "Evaluating Hydrologic Reservoir Constraint in Coal Seams and Shale Formations" filed Apr. 7, 2011, the contents of the application which is hereby incorporated herein by reference in its entirety.

TECHNICAL FIELD

This disclosure provides a sensing method that evaluates levels of hydrologic constraint in aquifers occurring in unconventional reservoirs, such as shale formations and coal formations. Specifically, the disclosed sensing method measures levels of naturally-occurring $^{13}C$ in a reservoir and compares the level of $^{13}C$ to the levels typical for highly constrained and highly unconstrained reservoirs. The disclosed sensing method also monitors levels of naturally-occurring $^{13}C$ in a reservoir while operations that may unintentionally or intentionally change the constraint in a reservoir are undertaken. Such operations can include, for example, cementing of casing in a wellbore intersecting more than one reservoir, hydraulic fracturing of a reservoir, and horizontal drilling in a reservoir.

BACKGROUND

Isotopic analysis of reservoir fluids in coal seams is a method to evaluate the type of chemical process producing coal bed methane gas retrieved from those seams (Dudley D. Rice, George E. Claypool, *AAPG Bulletin*, Volume 65, Issue 1. (January), Pages 5-25 (1981)). This method is possible because methanogenic consortia that digest the coal to produce methane preferentially digest moieties containing $^{12}C$ atoms. Thus, gases produced by methanogens are enriched in $^{12}C$.

The preferential metabolysis of $^{12}C$ from coals or shales during biogenesis results in enrichment of $^{13}C$ in the carbon containing salts and other materials residual to the process. This enrichment has been used to typecast fluids from particular coal seams (Enhancing Microbial Gas From Unconventional Reservoirs: Geochemical And Microbiological Characterization Of Methane-Rich Fractured Black Shales, FINAL REPORT (March 2004-September 2004) Prepared by: Anna M. Martini, Klaus Nüsslein, Steven T. Petsch, Prepared for: RESEARCH PARTNERSHIP TO SECURE ENERGY FOR AMERICA, Subcontract No. R-520) and even to track the eventual impact of the fluids on the environment (http://faculty.gg.uwyo.edu/cfrost/pdfs/2010%20Frost%20CBNG%20book.pdf). But the enrichment of $^{13}C$ in the carbon containing salts and other materials residual to the preferential metabolysis of $^{12}C$ from coals or shales during biogenesis has not been used in the manner of the present disclosure, that is, to measure hydrologic constraint. These measurements are made while operations may be undertaken that unintentionally or intentionally change the constraint in a reservoir. More specifically, "hydrologic constraint" refers to the extent to which the fluids resident in a coal seam or shale formation are residual from the methanogenic process. Thus, highly constrained reservoirs have little or no influx of foreign fluids that are not residual from the methanogenic process. Highly unconstrained reservoirs have appreciable, and sometimes significant, influx of foreign fluids that are not residual from the methanogenic process. Such foreign fluids can include, but are not limited to, fluids from other geological formations, fluids from surface waters, fluids from recharge at formation outcrop, and others. Influx of such fluids can occur by a variety of mechanisms including, but not limited to, via a wellbore connecting multiple formations, via a multi-formation geological fault, and via fracture networks connected to similar cross formation flow pathways.

Coal is the result of coalification, which pertains to the degree of biogenic and then thermogenic transformation of organic sediments. Coalification occurs initially via methanogens. Methanogens perform methanogenesis, a type of biogenic process, which results in enrichment of $^{13}C$ isotope because $^{12}C$ is consumed as it is easier to metabolize. Thermogenesis however, does not affect $^{13}C$ levels to a significant extent. Moreover, surface water generally has non-enriched $^{13}C$ levels. Gases produced by thermogenic processes, on the other hand, undergo no such kinetic preferential metabolysis and therefore are not significantly enriched in $^{12}C$. As a result, measurement of $^{12}C$ levels in methane gas produced from coals can indicate whether the coal is undergoing biogenic or thermogenic coalification.

The natural abundance of $^{12}C$ isotopes is about 98.9% of carbon atoms. The natural abundance of $^{13}C$ isotope is about 1.1%. In water or an aqueous media, the dissolved inorganic carbon (DIC) consists of carbon dioxide/carbonic acids $[CO_2+H_2CO_3]$, bicarbonate $[HCO_3^-]$ and carbonate $[CO_3^{2-}]$. Therefore, the tracer of interest is $\delta^{13}C_{DIC}$, which is defined as the $^{13}C/^{12}C$ ratio in the sample divided by the standard $^{13}C/^{12}C$ ratio, minus one, and typically expressed in parts per thousand by then multiplying the result by one thousand. In coal beds, bacteria ferment acetate $(CH_3COOH \rightarrow CH_4+CO_2)$ and reduce carbon dioxide $(CO_2+4H_2 \rightarrow CH_4+2H_2O)$. As a result, bacterial methanogenesis preferentially removes $^{12}C$ and the remaining DIC is enriched in $^{13}C$.

A positive $\delta^{13}C_{DIC}$ identifies groundwater in which biogenic production of methane has occurred. The $\delta^{13}C_{DIC}$ of groundwater that is not associated with methanogenesis have ratios of negative 5% to negative 20%, whereas water coproduced with coal bed methane has ratios as high as +35%.

Therefore, there is a need in the art for methods using $\delta^{13}C$ enrichment measurements in coal and shale fluids to indicate practical reservoir characteristics of commercial importance, such as hydrologic constraint in aquifers. There is also a need for sensor devices that can perform such measurements rapidly and effectively in coal bed and shale fluid reservoirs. The present disclosure was made to address this need.

SUMMARY

The present disclosure provides a method for determining hydrologic constraints in unconventional reservoirs, comprising:

(a) determining levels of naturally-occurring $^{13}C$ in a typical unconventional reservoir;

(b) determining the level of $^{13}C$ in a target unconventional reservoir; and (c) comparing the $^{13}C$ levels between a typical unconventional reservoir to a target unconventional reservoir to show if there have been changes to hydrologic constraint from one or a plurality of operations in the target unconventional reservoir. For purposes of this disclosure, a typical unconventional coalbed methane reservoir may have ratios of $\delta^{13}C_{DIC}$ as high as +35‰. A target unconventional reservoir is a coalbed or shale reservoir under investigation using the methods and apparatus of this disclosure.

Preferably, the unconventional reservoirs are coal bed reservoirs and shale fluid reservoirs. Preferably, the operations in the target unconventional reservoir are selected from the group consisting of cementing of casing in a wellbore intersecting more than one reservoir, hydraulic fracturing of a reservoir, horizontal drilling in a reservoir, and combinations thereof.

The present disclosure further provides a method for determining hydrologic constraints in unconventional reservoirs, comprising:

(a) determining levels of naturally-occurring $^{13}C$ in a typical Unconventional reservoir;

(b) determining the level of naturally-occurring $^{13}C$ in a target unconventional reservoir; and (c) comparing the levels of $^{13}C$ between the typical unconventional reservoir and the target unconventional reservoir to determine whether the target unconventional reservoir has less reservoir constraints than the typical unconventional reservoir.

Preferably, the unconventional reservoirs are coal bed reservoirs or shale fluid reservoirs. Preferably, a difference in respective levels of $^{13}C$ between the typical and the target reservoirs is used to predict future production success or failure of the target reservoir. Preferably, the levels of $^{13}C$ are determined by use of Raman spectroscopy. Preferably, the operations in the target unconventional reservoir are selected from the group consisting of cementing of casing in a wellbore intersecting more than one reservoir, hydraulic fracturing of a reservoir, horizontal drilling in a reservoir, and combinations thereof. More preferably, the levels of $^{13}C$ are compared to the levels of levels of $^{12}C$ in order to produce a $\delta^{13}C$ enrichment level.

The present disclosure further provides a method for determining hydrologic constraints in unconventional reservoirs, comprising:

(a) determining or obtaining levels of naturally-occurring $^{13}C$ in a typical unconventional reservoir;

(b) determining the level of $^{13}C$ in a target unconventional reservoir a plurality of times; and (c) comparing the $^{13}C$ levels between the typical unconventional reservoir to the target unconventional reservoir each time to show if there have been changes to hydrologic constraint from one or a plurality operations in the target unconventional reservoir.

The present disclosure also provides a method for determining extent of hydraulic fracturing of a target unconventional reservoir, comprising:

(a) determining levels of naturally-occurring $^{13}C$ in a target unconventional reservoir;

(b) hydraulically fracturing the target unconventional reservoir to create a fractured reservoir;

(c) determining levels of $^{13}C$ in the fractured reservoir; and (d) comparing the levels of $^{13}C$ in the target unconventional reservoir of step (a) to the fractured reservoir of step (c) to evaluate determine if non-reservoir fluids have begun entering the reservoir as a measure of extent of hydraulic fracturing.

Preferably, the unconventional reservoirs are coal bed reservoirs or shale fluid reservoirs. Preferably, a difference in respective levels of $^{13}C$ in the target reservoir before and after fracturing is used to predict future production success or failure of the target reservoir. Preferably, the levels of $^{13}C$ are determined by use of Raman spectroscopy. Preferably, the levels of $^{13}C$ are compared to the levels of levels of $^{12}C$ in order to produce a $\delta^{13}C$ enrichment level.

BRIEF DESCRIPTION OF THE FIGURES

The accompanying drawings, which are incorporated in and constitute a part of the specification, illustrate preferred embodiments of the invention. These drawings, together with the general description of the invention given above and the detailed description of the preferred embodiments given below, serve to explain the principles of the invention.

DETAILED DESCRIPTION

Without being bound by theory, the hypothesis underpinning the disclosed method is that coals contain $^{13}C$ enriched fluids. The level of $\delta^{13}C$ enrichment is a characteristic of each zone and field. Moreover, surface and non-coal aquifers do not have $^{13}C$ enriched aqueous fluids. Therefore, measuring $^{13}C$ levels confirms if an aqueous fluid comes from a coal bed. Further, any measured decrease in $\delta^{13}C$ enrichment from a baseline measurement is thus directly proportional to an influx of aqueous fluid from non-coal zones. As a result, the disclosed method is novel and has not been employed during commercial exploration and production of coal bed methane and shale gas.

The present disclosure provides a new reservoir evaluation technology that allows operators to high grade prospective shale and coalbed gas properties and target pay zones, allowing operators to avoid non-economic completion costs and water use. By providing a method and apparatus that can be used to quickly, accurately and inexpensively assess shale and coalbed gas resources at a high data density, this disclosure enables more complete evaluation of shale and coalbed gas resources. This evaluation focuses operators on developing completion methods for shale and coalbed gas targets that warrant investment, reduce overall water usage, and increase the conversion of shale and coalbed gas resources into shale and coalbed gas reserves. The disclosed method removes uncertainty regarding possible fluid influx into reservoirs via recharge or invasion, incenting more rapid capital investment by shale and coalbed gas operators and investors, and accelerating natural gas production from these reservoirs. The disclosed method enables shale and coalbed gas operators to increase exploration success rates, reduce finding costs, reduce completion costs, and reduce environmental impacts without constraining production.

Methods for Determining $^{13}C$ Levels

Typical methods for measuring the relative levels of $^{12}C$ and $^{13}C$ in fluids produced from coals and shales involve the use of various type of mass spectrometer laboratory instruments. In order to employ such methods, it is necessary to 1. collect fluid samples from a zone of interest, or from wells completed in a zone of interest and producing fluid from that zone;
2. insure that such samples are not affected by subsequent oxidation or other spurious chemical processes or contaminants;
3. transport such samples to a laboratory equipped with appropriate analytical equipment;
4. analyze the samples for $^{12}C$ and $^{13}C$ levels; and
5. compare those levels to the levels typical or expected for the zone of interest in order to ascertain hydrological constraint in the zone of interest.

This ex situ process is tedious, time consuming, costly and limited in nature. Analysis of multiple fluid samples is difficult and therefore evaluation of how fluid properties may vary over time is not facilitated by this method. Therefore, a need exists for a method for measuring the relative levels of $^{12}C$ and $^{13}C$ in fluids produced from coals and shales that operates in situ.

Disclosed herein is a method of using an optical spectrometer to measure in situ the relative levels of $^{12}C$ and $^{13}C$ in fluids produced from coals and shales. This method involves measuring the fundamental vibrational frequencies for molecular bonds and moieties in carbon containing salts. Such vibrational frequencies depend on the weight of the atoms participating in the vibrational moments. Thus, the fundamental vibrational frequencies of $^{12}C$ containing molecular bonds occur at higher energies than the fundamental vibrational frequencies of $^{13}C$ containing molecular bonds and moieties.

A variety of optical spectroscopies, including but not limited to Raman spectroscopy, infrared spectroscopy, and near-infrared spectroscopy, measure the fundamental vibrational frequencies, or combinations of fundamental vibrational frequencies, in molecules.

Figure 1:
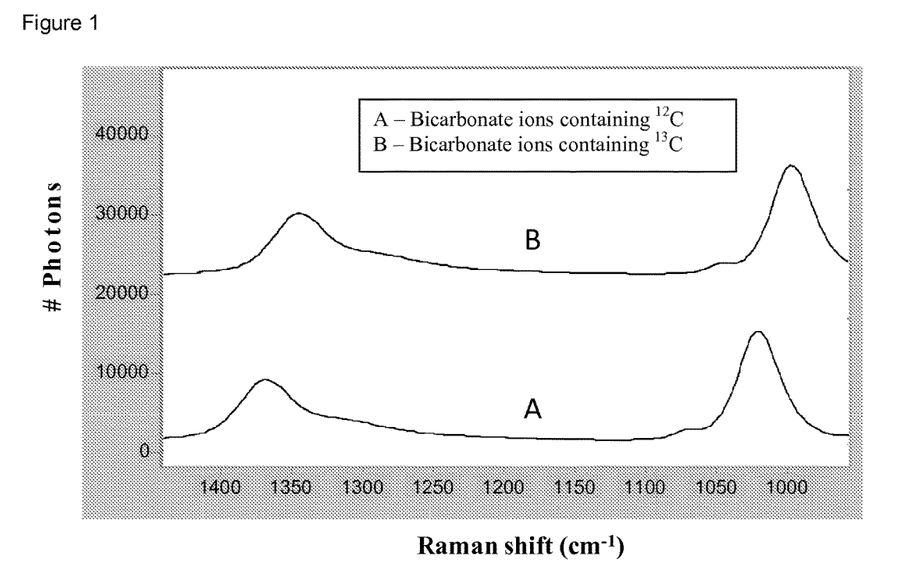
FIG. 1 shows representative Raman spectra of the bicarbonate ion containing (A) $^{12}C$ and (B) $^{13}C$ atoms dissolved in water.

In Raman spectroscopy, the shift in vibrational frequency between $^{12}C$ and $^{13}C$ is approximately proportional to the vibrational shift expected for a spring connecting two masses, where one mass is increased in mass from 12 mass units to 13 mass units. For bicarbonate, the reduction in vibrational frequency for a molecule containing $^{13}C$ (as compared to a molecule containing $^{12}C$) is about 1.8% or about 20 wavenumbers. Representative spectra of both $^{12}C$ and $^{13}C$ containing bicarbonate ion dissolved in water are shown in FIG. 1.

Therefore, a Raman spectrometer capable of resolving the $^{12}C$ and $^{13}C$ peaks, and detecting accurately changes in the relative sizes of those peaks, can be used to measure the relative $\delta^{13}C$ enrichment in coal seam and shale gas reservoir fluids.

Raman spectroscopy has been successfully adapted for use in coal seam and shale gas wells, as set forth in previously incorporated U.S. Pat. No. 6,678,050 to Pope et al. Therefore, this invention discloses for the first time the use of Raman spectrometers to measure $^{13}C$ enrichment levels in situ, downhole, in coal seam and shale gas wells.

Likewise, Raman spectroscopy has been successfully adapted for use in analyzing at the wellhead fluids produced from coal seam and shale gas reservoirs. See pending application entitled In-Situ Detection And Analysis Of Methane In Coal Bed Methane Formations With Spectrometers, Ser. No. 61/602,939, filed Feb. 24, 2012 which is incorporated in its entirety by reference herein. Therefore, this invention discloses for the first time the use of Raman spectrometers to measure $\delta^{13}C$ enrichment levels in situ, at the wellhead, in coal seam and shale gas fluid discharge streams.

In a preferred embodiment, a Raman spectrometer suitable for use in a well is obtained using previously disclosed inventions. One such Raman spectrometer is the device used by the assignee, which is an epi-illuminated, grating equipped Raman spectrometer with a 532 nm laser excitation and charge-coupled device (CCD) detector packaged into a 3-inch diameter, 80 inch long high pressure steel housing. The spectrometer interrogates the surrounding gases or fluids via a one-inch sapphire window located at bottom of its housing. The spectrometer communicates to a surface computer and power unit via a standard four-conductor wireline.

The Raman spectrometer wireline tool top sub is connected to a cable head that is connected to a four-conductor wireline spool of appropriate length. The spectrometer is powered up by connecting a power supply to two of the four wires in the wireline. The surface computer communicates with and controls the spectrometer via the other two wires.

The spectrometer is operated at the wellhead in order to check its operation and calibration. It is then lowered into the well while Raman spectra are collected at 10 second intervals and then transmitted to the surface computer over a subsequent 20 seconds. When the spectrometer encounters reservoir fluid in the wellbore, the Raman spectrum characteristic of that fluid is measured and transmitted to the surface computer. The human operator reviews that spectrum for quality and character to confirm its origin, and the computer processes that spectrum for spectral features of interest, such as position of peaks and number of photons comprising one or more particular peaks.

In a well containing $^{12}C$ and $^{13}C$ isotopes of particular chemicals, such as dissolved bicarbonate, the Raman spectrometer measures one position and number of photons comprising a $^{12}C$-related bicarbonate vibrational mode and a different position and number of photons comprising a peak corresponding to the $^{13}C$-related bicarbonate vibrational mode. The human operator and/or the computer then evaluate the positions and number of photons for each peak and relate them to each other and/or to a calibration scale measured under controlled laboratory conditions. In this manner, the amount of $\delta^{13}C$ enrichment in a reservoir fluid is quickly and conveniently measured in a wellbore.

Figure 2:
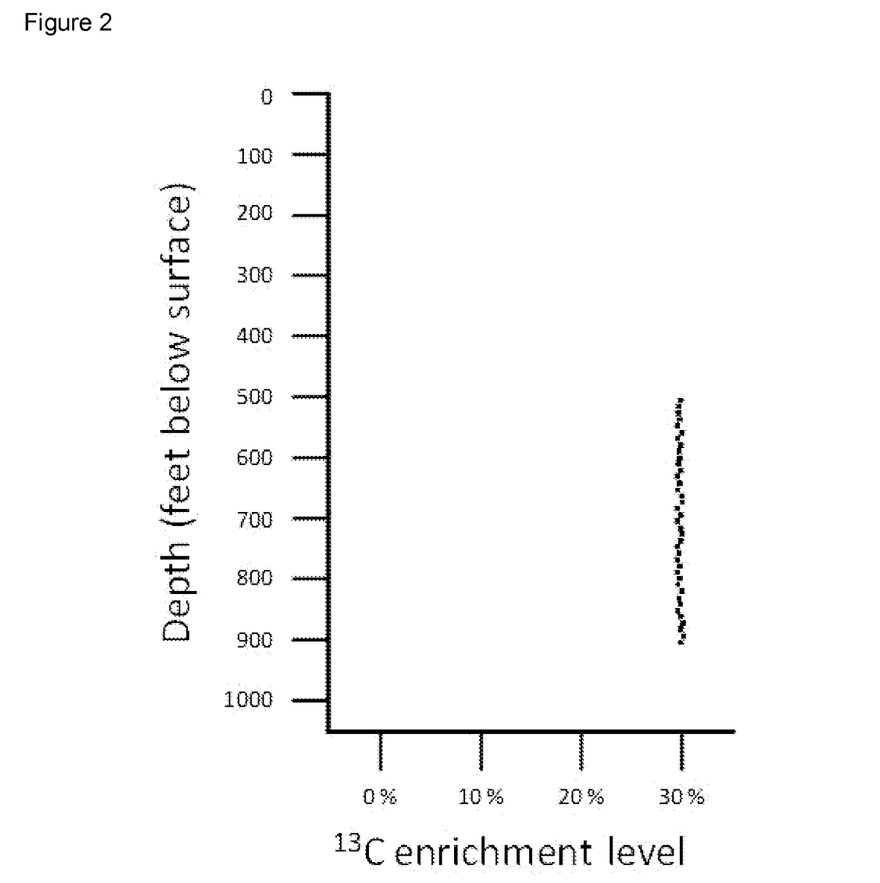
FIG. 2 shows a representative log of $\delta^{13}C$ enrichment in naturally occurring bicarbonate ions dissolved in reservoir fluid, as measured downhole using a Raman spectrometer in a coalbed methane well.

For example, a five inch diameter steel casing was completed into a twelve-foot thick coal seam by perforation of the casing. The coal seam was located at 890 feet below surface to 902 feet below surface. Perforations were made from 892 feet below surface to 900 feet below surface. The perforations were performed with 50 feet of water cushion above the perforating gun. The coal seam subsequently flowed 340 feet of additional fluid into the wellbore, so that the wellbore contained 390 feet of fluid total above the mean depth of the coal seam. The top of the fluid column was therefore located at 506 feet below surface. A three-inch diameter, 80 inch long wireline Raman spectrometer tool was subsequently lowered into the wellbore while it was continuously collecting Raman spectra. When it encountered fluid in the wellbore, the Raman spectrometer subsequently collected and transmitted Raman spectra of that fluid (primarily water) and of the analytes in that fluid (primarily methane and bicarbonate containing both $^{12}C$ and $^{13}C$ isotopes). The spectra were then processed by the computer according to algorithms well known to those skilled in the art of vibrational spectroscopy to produce the concentrations of each bicarbonate isotope at each measured depth. Those concentrations were then mathematically compared to produce a 30% average $\delta^{13}C$ enrichment in the dissolved bicarbonate present at each depth in the fluid column, as shown in FIG. 2. The self consistent character of the resulting data at 556 feet below surface reflects the fact that the wellbore contained reservoir fluid at depths greater than 556 feet below surface. This fact was corroborated by examination of the methane concentration and total dissolved solids measured concurrently throughout the fluid column. Based on this result, the coal seam in which that well was completed was judged to be highly constrained. Since the methane gas content measured for the coal seam was of economic quantities, and since the drawdown required to produce gas from the coal seam was measured to be only 145 psia, the coal seam was judged to be an attractive production target.

Similar measurements can be undertaken using a variety of fluid handling techniques. For example, the example analysis described above could also be undertaken for multiple coal seams intersected by a cased and cemented wellbore where the casing is perforated sequentially starting with the deepest coal and fluid from each zone is isolated in the casing using an bridge plug, inflation packer, or similar device and Raman spectroscopy testing of $\delta^{13}C$ enrichment is subsequently undertaken on each isolated fluid.

In a further example, the example analysis described above could also be undertaken for multiple coal seams intersected by a cased and cemented wellbore where the casing is perforated in all zones and then the fluid from each zone is isolated and produced using a drill stem testing string, straddle packer, or similar device and Raman spectroscopy testing of $\delta^{13}C$ enrichment is subsequently undertaken on each isolated fluid.

In a further example, the example analysis described above could also be undertaken for multiple coal seams intersected by an uncased wellbore where each seam is isolated and fluid from each seam is produced using a drill stem testing string, straddle packer, or similar device and Raman spectroscopy testing of $\delta^{13}C$ enrichment is subsequently undertaken on each isolated fluid.

In a further example, the example analysis described above could also be undertaken wherein the Raman spectroscopy testing of $\delta^{13}C$ enrichment is performed using a Raman spectrometer located at the wellhead that is connected to a fiber optic assembly that is subsequently lowered into the wellbore to contact the fluid. The Raman spectroscopy analysis is then undertaken using the fiber optic assembly to deliver the excitation radiation and collect the scattered photons.

In some cases, it may be useful to compare the $\delta^{13}C$ enrichment measurements described herein with standard water, gas and coal analysis results in order to describe more comprehensively the coal seam or shale gas reservoir. Such comparison can assist in interpretation of the data sets. The combination of such analyses with the $\delta^{13}C$ enrichment measurements described herein is considered a part of the invention disclosed here.

Methods of Using Determined $^{13}C$ Levels

This invention discloses for the first time the use of $\delta^{13}C$ enrichment data to assess whether drilling and completion operations create new flow channels for fluids between the target coal or shale zone and other zones near a wellbore. In particular, this invention describes a method of testing an untreated coal or shale zone in order to establish its naturally characteristic $\delta^{13}C$ enrichment level, treating the coal or shale zone, retesting the coal or shale zone to evaluate whether the treatment created new fluid flow channels to other zones, and then using that information to determine whether the coal or shale zone is an appropriate production target. That information can also be used to determine whether the treatment resulted in contamination to the surrounding zones. That information can also be used to refine the treatment itself in order to reduce or eliminate said contamination.

Figure 3:
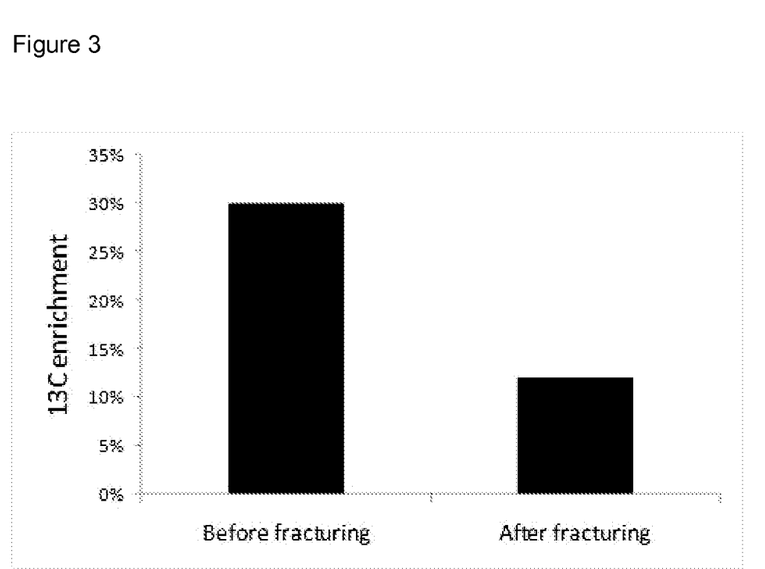
FIG. 3 shows a representative graph of $\delta^{13}C$ enrichment for reservoir fluids produced from a coal seam before and after hydraulic fracturing was completed on the coal seam. The decrease in $\delta^{13}C$ enrichment after hydraulic fracturing indicated that the induced fractures connected to one or more adjoining fluid reservoirs, thereby reducing the coal seam's hydraulic constraint, increasing the fluid volumes necessary to be produced in order to produce gas from the coal seam, and injecting hydraulic fracturing fluids and chemicals into the adjoining fluid reservoir or reservoirs.

For example, a five inch diameter steel casing was completed into a twelve-foot thick coal seam by perforation of the casing. The coal seam was located at 890 feet below surface to 902 feet below surface. Perforations were made from 892 feet below surface to 900 feet below surface. The perforations were performed with 50 feet of water cushion above the perforating gun. The coal seam subsequently flowed 340 feet of additional fluid into the wellbore, so that the wellbore contained 390 feet of fluid total above the mean depth of the coal seam. The top of the fluid column was therefore located at 506 feet below surface. A three-inch diameter, 80 inch long wireline Raman spectrometer tool was subsequently lowered into the wellbore while it was continuously collecting Raman spectra. When it encountered fluid in the wellbore, the Raman spectrometer subsequently collected and transmitted Raman spectra of that fluid (primarily water) and of the analytes in that fluid (primarily methane and bicarbonate containing both $^{12}C$ and $^{13}C$ isotopes). The spectra were then processed by the computer according to algorithms well known to those skilled in the art of vibrational spectroscopy to produce the concentrations of each bicarbonate isotope at each measured depth. Those concentrations were then mathematically compared to produce a 30% average $\delta^{13}C$ enrichment in the dissolved bicarbonate present at each depth in the fluid column, as shown in FIG. 2. The self consistent character of the resulting data at 556 feet below surface reflects the fact that the wellbore contained reservoir fluid at depths greater than 556 feet below surface. This fact was corroborated by examination of the methane concentration and total dissolved solids measured concurrently throughout the fluid column. Based on this result, the coal seam in which that well was completed was judged to be highly constrained. Since the methane gas content measured for the coal seam was of economic quantities, and since the drawdown required to produce gas from the coal seam was measured to be only 145 psia, the coal seam was judged to be an attractive production target. Hydraulic fracturing of the coal seam was undertaken in order to increase its effective permeability in order to increase its water and gas flow rates. 30,000 barrels of fluid were injected into the seam at 1,500 psia in order to fracture the seam. Subsequently, fluid was produced back until the solution gas and salinity measured for the fluid became constant, indicating that the frac fluids had all been removed from the formation and the produced fluid was reservoir fluid. Subsequently, fluid was sampled from the water discharge pipe and conveyed to a laboratory where $\delta^{13}C_{DIC}$ was measured to be 12% enriched. FIG. 3 shows a graph of the $\delta^{13}C_{DIC}$ in fluids collected from the coal seam before and after hydraulic fracturing. Because the post-frac fluid $\delta^{13}C_{DIC}$ was reduced substantially from the pre-frac $\delta^{13}C_{DIC}$ level, it was concluded that the hydraulic fracturing process fractured through the coal seam and into an overlaying limestone.

One group of Atlantic Rim springs have positive $\delta^{13}C_{DIC}$. Enriched Lewis shale springs have Na—HCO$_3$-type water, and some of them emit methane. Enriched Lewis shale springs have higher total dissolved contents (TDS) of 800-4000 mg/L than springs with negative $\delta^{13}C_{DIC}$ (TDS typically 1064<1000 mg/L). These springs occur together in clusters up dip of the coal bed natural gas (CBNG) production areas. The variations in abundance of methane emerging from these springs may be related to local variations in hydrostatic pressure of the near-surface methane-bearing reservoirs or influx from other gas-saturated coal bed reservoirs. Although water produced with CBNG are Na—HCO$_3$-type water with relatively high TDS (>1000 mg/L) and positive $\delta^{13}C_{DIC}$. Water samples from wells with low water/gas ratios have the highest $\delta^{13}C_{DIC}$ and produce the most gas. Water samples from wells with lower, although still positive, $\delta^{13}C_{DIC}$ values reflect the addition of isotopically light water from other reservoirs. Structure contour mapping identifies faults in proximity to low $\delta^{13}C_{DIC}$ wells. Geochemical analysis of $\delta^{13}C_{DIC}$ help to identify CBNG and shale natural gas reservoirs with the highest potential for natural gas production while minimizing unnecessary water production.

The present disclosure predicts a correlation between water/gas ratios, production potential, efficiency, and $\delta^{13}C_{DIC}$. $\delta^{13}C_{DIC}$ should be less enriched in coal bed reservoirs that are hydraulically connected to multiple water sources with isotopically light carbon compositions. An unconfined coal bed reservoir is likely to produce more water during CBNG production than a confined coal bed reservoir, as the hydraulic pressure of multiple connected reservoirs would need to be reduced to promote CBNG desorption. A group of wells in a single coal bed, which have highly enriched $\delta^{13}C_{DIC}$ values and low cumulative water/gas ratios, appear to be producing from confined coal bed reservoirs. Another group of wells, which are not as enriched regarding $\delta^{13}C_{DIC}$ and have high cumulative water/gas ratios, are likely producing from partially confined or unconfined coal bed reservoirs. $\delta^{13}C_{DIC}$ may help producers determine in which geographic areas coal bed reservoir water has undergone the most biologic methanogenic activity and/or those coal bed reservoirs that are confined.

Enrichment of $\delta^{13}C_{DIC}$ is directly related to bacterial methanogenesis. The generation of thermogenic gas will not enrich DIC ratios, and $\delta^{13}C_{DIC}$ characterization is inapplicable in CBNG reservoirs that are exclusively thermogenic. The $\delta^{13}C_{DIC}$ alone cannot identify which specific isotopically light reservoirs are in communication with coal bed reservoirs. Water quality, well log, and geologic interpretation of likely reservoirs may aid in distinguishing these reservoirs.

Figure 4:
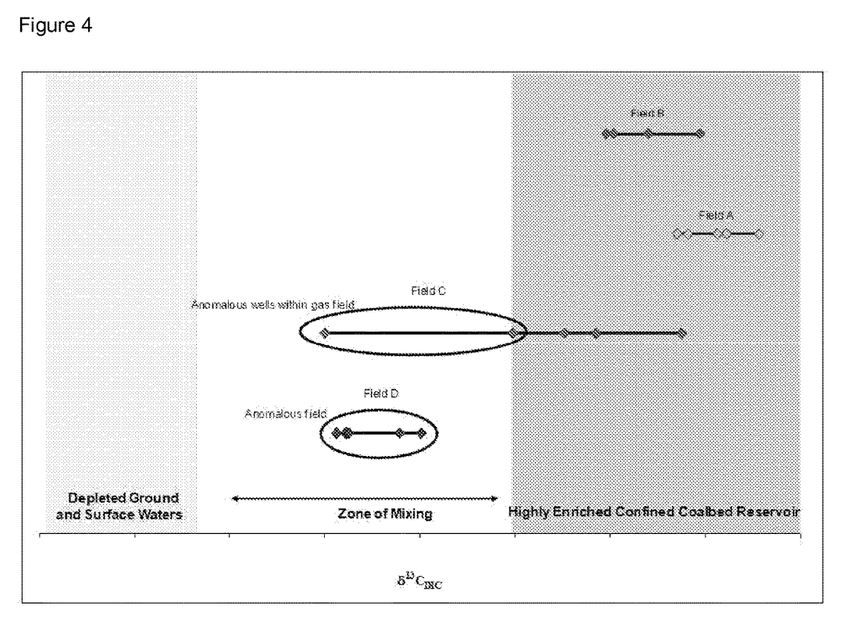
FIG. 4 graphs positive $\delta^{13}C_{DIC}$ measurement in produced waters from various coalbed reservoirs, showing particularly highly enriched $^{13}C$ quantities in fields A and B of 4 fields (A through D).
Figure 5:
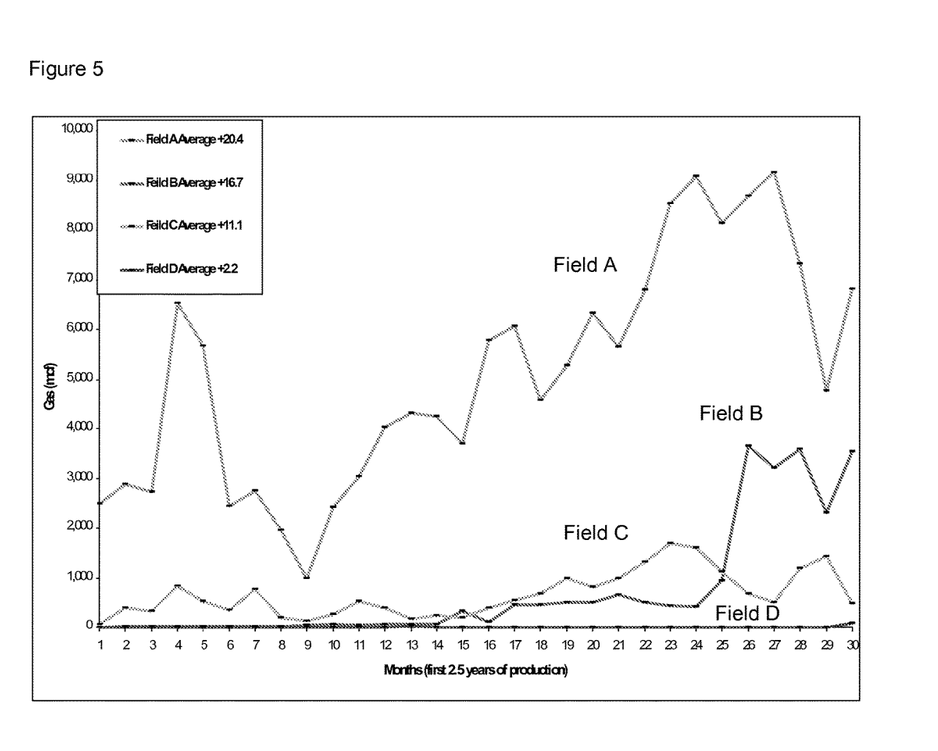
FIG. 5 graphs gas production from 4 fields over 2.5 years.

A $\delta^{13}C_{DIC}$ measurement can characterize CBNG reservoirs. Moreover, carbon isotopic tracers in produced water can guide CBNG development to those areas where natural gas production is maximized and water production is minimized. Positive $\delta^{13}C_{DIC}$ of CBNG produced water indicates that bacterial methanogenesis is associated with these waters (FIG. 4). However, a significant range in $\delta^{13}C_{DIC}$ exists in Field A CBNG samples, which provides additional information about the potential for CBNG production from individual wells and related reservoirs (FIG. 5).

Analyte concentrations also increase with distance from faults. These measurements can determine if CBNG reservoirs and shale bed natural gas (SBNG) reservoirs in a particular area are partially confined or unconfined as a result of faulting. This is because water with isotopically light carbon compositions and lesser amounts of brine to mix into the coal bed reservoir.

Figure 6:
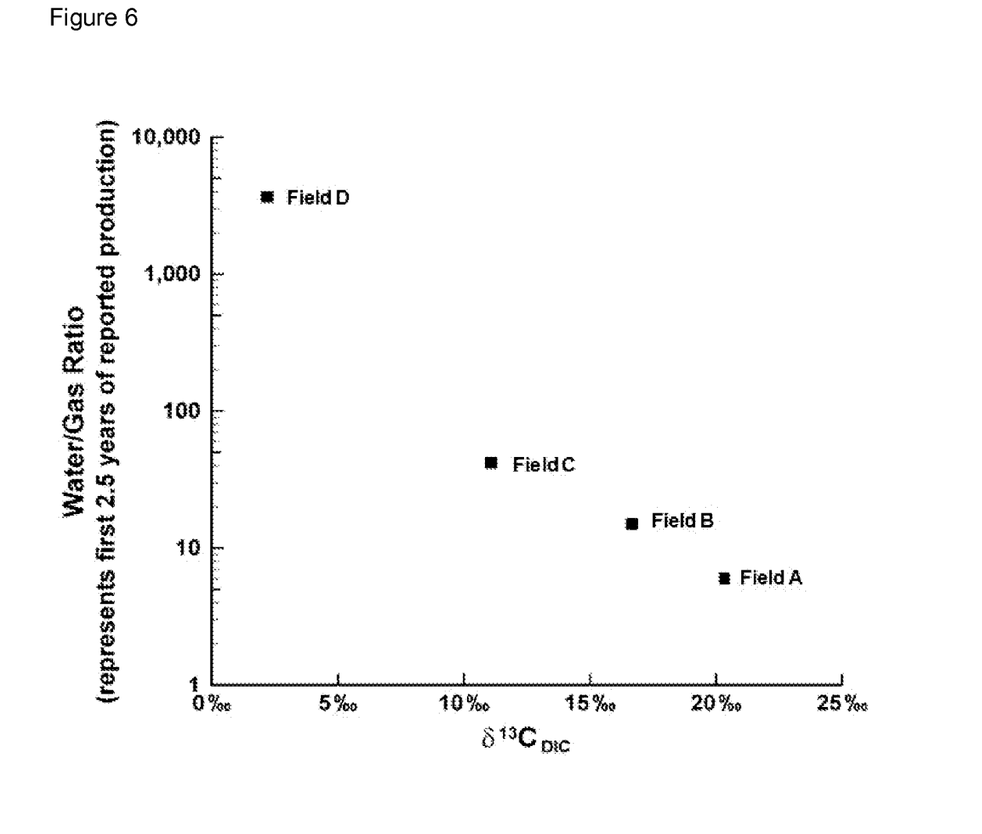
FIG. 6 graphs the water gas ratio of 4 fields (A through D) as a function of $\delta^{13}C_{DIC}$.

$\delta^{13}C_{DIC}$ measurements can analyze CBNG production potential, particularly in hydraulically confined CBNG reservoirs. This capability alone makes $\delta^{13}C_{DIC}$ a significant coal bed reservoir and CBNG analysis tool (FIG. 6). A correlation is predicted between water/gas ratios, production potential, efficiency, and $\delta^{13}C_{DIC}$, as: (a) $\delta^{13}C_{DIC}$ should be less enriched in coal bed reservoirs that are hydraulically connected to multiple water sources with isotopically light carbon compositions. (b) An unconfined coal bed reservoir is likely to produce more water during CBNG production than a confined coal bed reservoir, as the hydraulic pressure of multiple connected reservoirs would need to be reduced to promote CBNG desorption.

Enrichment of $\delta^{13}C_{DIC}$ is directly related to bacterial methanogenesis. The generation of thermogenic gas will not enrich DIC ratios, and $\delta^{13}C_{DIC}$ characterization is inapplicable in CBNG reservoirs that are exclusively thermogenic. $\delta^{13}C_{DIC}$ alone cannot identify which specific isotopically light reservoirs are in communication with coal bed reservoirs. Water quality, strontium isotopic compositions, well log, and geologic interpretation of likely reservoirs may aid in distinguishing these reservoirs. $\delta^{13}C_{DIC}$ analysis records the characteristics of the produced water at the time the wells were sampled.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

This specification is to be construed as illustrative only and is for the purpose of teaching those skilled in the art the manner of carrying out the invention. It is to be understood that the forms of the invention herein shown and described are to be taken as the presently preferred embodiments. As already stated, various changes may be made in the shape, size and arrangement of components or adjustments made in the steps of the method without departing from the scope of this invention. For example, equivalent elements may be substituted for those illustrated and described herein and certain features of the invention maybe utilized independently of the use of other features, all as would be apparent to one skilled in the art after having the benefit of this description of the invention.

While specific embodiments have been illustrated and described, numerous modifications are possible without departing from the spirit of the invention, and the scope of protection is only limited by the scope of the accompanying claims.

We claim:

1. A method for determining hydrologic constraints in reservoirs, comprising:
   a. determining an expected level of naturally-occurring $^{12}C$ and $^{13}C$ isotopes in a reservoir using a Raman spectroscopy instrument placed downhole and in communication with a computer for data analysis;
   b. determining a measured level of naturally-occurring $^{12}C$ and $^{13}C$ isotopes in a target reservoir using the Raman spectroscopy instrument placed downhole and in communication with the computer for data analysis;
   c. comparing the expected and measured levels of $^{12}C$ and $^{13}C$;
   d. the computer calculating concentrations of $^{12}C$ and $^{13}C$ isotopes at each measured depth; and e. comparing the levels determined in steps a. and b. to determine the relative hydrologic constraint of the target reservoir;

wherein step e. comprises determining $\delta^{13}C_{DIC}$, where $\delta^{13}C_{DIC}=[[(^{13}C/^{12}C)_{measured}/(^{13}C/^{12}C)_{expected}]-1] \times 1000$; and wherein the Raman spectroscopy instrument comprises an epi-illuminated Raman spectrometer comprising a high pressure steel tube with a diameter less than 5 inches, a sapphire window at a bottom end of a housing to irradiate samples, a laser excitation source, and a charge-coupled device detector.

2. The method of claim 1, wherein an analyte is subjected to Raman spectroscopy, the analyte comprising dissolved inorganic carbon (DIC) containing both $^{12}C$ and $^{13}C$ isotopes.

3. The method of claim 1, wherein the Raman spectroscopy instrument is continuously collecting Raman spectra.

4. The method of claim 1, wherein the Raman spectroscopy instrument collects Raman spectra at least once every 60 seconds.

5. The method of claim 1 wherein the levels of $^{13}C$ in the target reservoir are compared to the levels of $^{12}C$ in the target reservoir to produce a $^{13}C$ enrichment level of the target reservoir.

6. The method of claim 1, wherein the reservoir and the target reservoir are coal bed reservoirs or shale fluid reservoirs.

7. The method of claim 1, further comprising using a difference in respective levels of $^{12}C$ and $^{13}C$ isotopes between the reservoir and the target reservoir to predict gas production levels of the target reservoir.

8. The method of claim 1, further comprising performing an operation in the target reservoir, wherein the operation in the target reservoir comprises at least one of cementing of casing in a wellbore intersecting the target reservoir, hydraulic fracturing of the target reservoir, and horizontal drilling in the target reservoir.

9. The method of claim 8, wherein the levels of $^{13}C$ are compared to the levels of $^{12}C$ in order to produce a $^{13}C$ enrichment level.

* * * * *